United States Patent [19]

Picard et al.

[11] Patent Number: 5,245,068

[45] Date of Patent: Sep. 14, 1993

[54] OXYSULFONYL CARBAMATES

[75] Inventors: Joseph A. Picard; Drago R. Sliskovic, both of Ypsilanti, Mich.

[73] Assignee: Warner-Lambert Company, Morris Plains, N.J.

[21] Appl. No.: 15,662

[22] Filed: Feb. 9, 1993

Related U.S. Application Data

[63] Continuation of Ser. No. 738,772, Aug. 1, 1991, abandoned, which is a continuation-in-part of Ser. No. 606,006, Oct. 30, 1990, abandoned.

[51] Int. Cl.$^5$ .......................................... C07C 303/00
[52] U.S. Cl. .................................................... 558/49
[58] Field of Search ................. 558/49; 514/481, 485, 514/488, 489, 490

[56] References Cited

FOREIGN PATENT DOCUMENTS 940292 3/1956 Fed. Rep. of Germany .

*Primary Examiner*—Alan Siegel
*Attorney, Agent, or Firm*—Michael J. Atkins

[57] ABSTRACT

The present invention is directed to compounds of the following general Formula I, methods for using the compounds of Formula I, pharmaceutical compositions thereof, and processes for preparing the compounds.

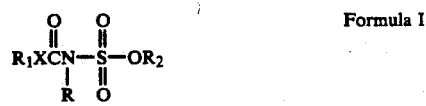

Formula I wherein X is oxygen or sulfur; wherein R is hydrogen, a straight or branched alkyl group having from 1 to 8 carbon atoms or benzyl; wherein each of $R_1$ and $R_2$ is phenyl, substituted phenyl, naphthyl, substituted naphthyl, an aralkyl group, a 5- or 6-membered monocyclic or fused bicyclic heterocyclic group, or a hydrocarbon chain having from 1 to 20 carbon atoms and from 1 to 3 double bonds.

9 Claims, No Drawings

OXYSULFONYL CARBAMATES

CROSS-REFERENCE TO RELATED APPLICATION

This application is a continuation of application Ser. No. 738,772, filed Aug. 1, 1991 which is a continuation-in-part of application Ser. No. 606,006, filed Oct. 30, 1990, both now abandoned.

BACKGROUND OF INVENTION

This invention relates to chemical compounds having pharmacological activity, to pharmaceutical compositions which include these compounds, and to a pharmaceutical method of treatment. More particularly, this invention concerns certain oxysulfonyl carbamates which inhibit the enzyme acylcoenzyme A:cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known cholesterol is transported in the blood in the form of complex particles consisting of a core of cholesteryl esters plus triglycerides and a variety of types of protein which ar recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE

German patent 940,292 dated Mar. 15, 1956 to Farbwerke Hoechst, AG describes the following compounds as being useful as textile assistants, pharmaceuticals and pesticides. No specific pharmaceutical use is described.

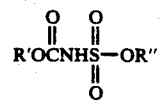

| R' | R" |
|---|---|
| $CH_3$ | Ph |
| $CH_3$ | 4-$NO_2$Ph |
| $C_2H_5$ | 4-$NO_2$Ph |
| $C_4H_9$ | 4-$NO_2$Ph |
| 4-Cl—Ph | 4-Cl—Ph |
| $CH_3$ | 4-Cl—Ph |

Chem. Ber. 96, 56–67 (1963) describes compounds of the following formula. No utility is described for these compounds.

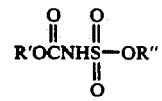

| R' | R" |
|---|---|
| $CH_3$ | 4-Cl—Ph |
| $CH_3$ | 4-$NO_2$Ph |
| $C_2H_5$ | 4-$NO_2$Ph |
| i-$C_3H_7$ | 4-Cl—Ph |
| n-$C_4H_9$ | 4-$NO_2$Ph |

Chem. Ber. 105, 2800–2804 (1972) describes compounds of the following formula. No utility is described for these compounds.

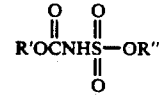

| R' | R" |
|---|---|
| 2,4,6-triCl—Ph | $CH_3$ |
| 2,6-di-Cl-4-Ph—Ph | n-$C_3H_7$ |
| 3,5-di-Cl-4-Ph—Ph | —$CH_2CH_2OCH_3$ |

Tetrahedron Letters describes the following two compounds no utility for which is described.

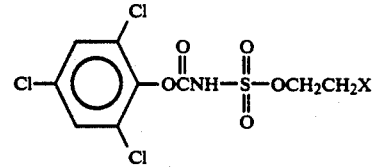

X = Cl or Br

SUMMARY OF THE INVENTION

The present invention is directed to compounds of the following general Formula I, methods for using the compounds of Formula I, pharmaceutical compositions thereof, and processes for preparing the compounds.

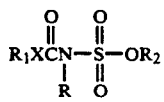

Formula I wherein X is oxygen or sulfur; wherein R is hydrogen, a straight or branched alkyl group having from 1 to 8 carbon atoms or benzyl; wherein each of $R_1$ and $R_2$ is selected from (a) phenyl which is unsubstituted or is substituted with from 1 to 3 substituents selected from
 phenyl,
 an alkyl group having from 1 to 6 carbon atoms and which is straight or branched,
 an alkoxy group having from 1 to 6 carbon atoms and which is straight or branched;
 phenoxy,
 hydroxy,
 fluorine,
 chlorine,
 bromine,
 trifluoromethyl,
 —COOH,
 —COOalkyl wherein alkyl has from 1 to 4 carbon atoms and is straight or branched,
 —$(CH_2)_pNR_3R_4$ wherein p is zero or one, and each of $R_3$ and $R_4$ is selected from hydrogen or a straight or branched alkyl group having 1 to 4 carbon atoms;

(b) 1- or 2-naphthyl which is unsubstituted or is substituted with from 1 to 3 substituents selected from
 phenyl,
 an alkyl group having from 1 to 6 carbon atoms and which is straight or branched,
 an alkoxy group having from 1 to 6 carbon atoms and which is straight or branched;
 hydroxy,
 phenoxy,
 fluorine,
 chlorine,
 bromine,
 nitro,
 trifluoromethyl,
 —COOH,
 —COOalkyl wherein alkyl has from 1 to 4 carbon atoms and is straight or branched,
 —$(CH_2)_pNR_3R_4$ wherein p, $R_3$ and $R_4$ have the meanings defined above;

(c) the group

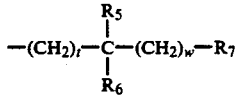

wherein t is zero or 1 to 4; w is zero or 1 to 4 with the proviso that the sum of t and w is not greater than 5; $R_5$ and $R_6$ are independently selected from hydrogen or alkyl having from 1 to 6 carbon atoms, or when $R_5$ is hydrogen, $R_6$ can be selected from the groups defined for $R_7$; and $R_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH_2)_pNR_3R_4$ wherein P, $R_3$ and $R_4$ have the meanings defined above;

(d) —$(CH_2)_s$—Q where in s is a number of from 0 to 3 and Q is a 5- or 6-membered monocyclic or fused bicyclic heterocycle containing at least 1 to 4 nitrogen, oxygen or sulfur atoms in at least one ring member; or (e) a straight or branched hydrocarbon chain having from 1 to 20 carbon atoms and which is saturated or contains from 1 to 3 double bonds; and pharmaceutically acceptable salts thereof with the proviso that:

(i) one of $R_1$ or $R_2$ is phenyl or substituted phenyl and
(ii) the following compounds are excluded:

| R' | R" |
| --- | --- |
| $CH_3$ | Ph |
| 4-ClPh | 4-ClPh |
| i-$C_3H_7$ | 4-ClPh |
| $CH_3$ | 4-ClPh |
| 2,4,6-triClPh | $CH_3$ |
| 2,6-di-Cl-4-Ph—Ph | n-$C_3H_7$ |

The present invention also provides a pharmaceutical composition for regulating cholesterol comprising an effective amount of a compound of the following general Formula II and a method of treating hypercholesterolemia and atherosclerosis comprising administering to a patient an effective amount of a compound of the following general Formula II with a pharmaceutically acceptable carrier.

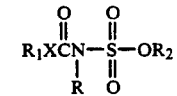

Formula II wherein X is oxygen or sulfur; wherein R is hydrogen, a straight or branched alkyl group having from 1 to 8 carbon atoms or benzyl; wherein each of $R_1$ and $R_2$ is selected from (a) phenyl which is unsubstituted or is substituted with from 1 to 3 substituents selected from
 phenyl,
 an alkyl group having from 1 to 6 carbon atoms and which is straight or branched,
 an alkoxy group having from 1 to 6 carbon atoms and which is straight or branched;
 phenoxy,
 hydroxy,
 fluorine,
 chlorine,
 bromine,
 nitro,
 trifluoromethyl,
 —COO H,
 —COOalkyl wherein alkyl has from 1 to 4 carbon atoms and is straight or branched,
 —$(CH_2)_pNR_3R_4$ wherein p is zero or one, and each of $R_3$ and $R_4$ is selected from hydrogen or a straight or branched alkyl group having 1 to 4 carbon atoms;

(b) 1- or 2-naphthyl which is unsubstituted or is substituted with from 1 to 3 substituents selected
 phenyl,
 an alkyl group having from 1 to 6 carbon atoms and which is straight or branched,
 an alkoxy group having from 1 to 6 carbon atoms and which is straight or branched;
 phenoxy, hydroxy,
fluorine,
chlorine,
bromine,
nitro,
trifluoromethyl,
—COOH,
—COOalkyl wherein alkyl has from 1 to 4 carbon atoms and is straight or branched,
—(CH$_2$)$_p$NR$_3$R$_4$ wherein p, R$_3$ and R$_4$ have the meanings defined above;
(c) the group

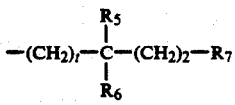

wherein t is zero or 1 to 4; w is zero or 1 to 4 with the proviso that the sum of t and w is not greater than 5; R$_5$ and R$_6$ are independently selected from hydrogen or alkyl having from 1 to 6 carbon atoms, or when R$_5$ is hydrogen, R$_6$ can be selected from the groups defined for R$_7$; and R$_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or (CH$_2$)$_p$NR$_3$R$_4$ wherein p, R$_3$ and R$_4$ have the meanings defined above;

(d) —(CH$_2$)$_s$—Q wherein s is a number of from 0 to 3 and Q is a 5- or 6-membered monocyclic or fused bicyclic heterocycle containing at least 1 to 4 nitrogen, oxygen or sulfur atoms in at least one ring member; or (e) a straight or branched hydrocarbon chain having from 1 to 20 carbon atoms and which is saturated or contains from 1 to 3 double bonds; and pharmaceutically acceptable salts thereof with the proviso that one of R$_1$ or R$_2$ is phenyl or substituted phenyl.

DETAILED DESCRIPTION OF THE INVENTION

The compounds of the present invention provide a novel class of oxysulfonyl carbamates which are ACAT inhibitors, rendering them useful in treating hypercholesterolemia and atherosclerosis.

In general Formulas I and II above, illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyl-dodecyl, 2-tetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

Illustrative examples of straight or branched alkyl groups having from 1 to 6 carbon atoms are as used in Formulas I and II include methyl, ethyl, n-propyl, isopropyl, n-pentyl, n-butyl, and tert-butyl.

A 5- or 6-membered monocyclic or fused bicyclic heterocycle is a monocyclic or fused bicyclic aromatic ring containing at least 1 to 4 heteroatoms in at least one ring, such as nitrogen, oxygen, or sulfur or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocycles containing a nitrogen atom.

More specifically, such a heterocycle may be a 2- or 3-thienyl; 2- or 3-furanyl; 2-, or 3-, or 4-pyridyl or -pyridyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-oxazolyl; 2-, 4-, or 5-thiazolyl, 3-, 4-, or 5-isoxazolyl; 3-, 4-, or 5-isothiazolyl; 5-tetrazolyl; 3- or 5-(1,2,4,-)triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Pharmaceutically acceptable salts of the compounds of Formulas I and II are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, J. Pharm. Sci. 66, 1-19 (1977).

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

Preferred compounds of the present invention are those wherein one of $R_1$ and $R_2$ is phenyl, and more preferably phenyl disubstituted in the 2,6-positions. Most preferably, both $R_1$ and $R_2$ are phenyl disubstituted in the 2,6-positions.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, *Biochemica et Biophysica* 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed in $IC_{50}$ values; i.e., the concentration of test compound required to inhibit the activity of the enzyme by 50%.

TABLE 1

| Example | IAI $IC_{50}$ ($\mu$M) |
| --- | --- |
| 1 | 29 |
| 2 | 90 |
| 3 | 95 |
| 4 | 52 |
| 5 | 13 |
| 6 | >100 |
| 7 | 40 |
| 8 | 13 |
| 9 | 12 |
| 10 | >10 |
| 17 | >50 |
| 18 | >50 |
| 19 | >50 |
| 20 | 50 |
| 21 | >50 |
| 22 | 38 |
| 23 | 10 |
| 24 | 50 |
| 25 | 6.4 |
| 26 | 30 |
| 27 | 3.3 |
| 28 | 5.2 |
| 30 | 48 |
| 31 | 63 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet (designated PCC) containing 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2.

TABLE 2

| Compound of Example | % Change (mg/dl) |
| --- | --- |
| 1 | −70 |
| 2 | −65 |
| 3 | −56 |
| 4 | −65 |
| 5 | −62 |
| 7 | −52 |
| 8 | −68 |
| 9 | −70 |
| 10 | −69 |
| 17 | −26 |
| 18 | −58 |
| 19 | −70 |
| 20 | −11 |
| 21 | −61 |
| 22 | +9 |
| 23 | −59 |
| 24 | −55 |
| 25 | −10 |
| 26 | −18 |
| 27 | −72 |
| 28 | −65 |
| 30 | −9 |
| 31 | −64 |

In therapeutic use as agents for treating hypercholesterolemia or atherosclerosis, the compounds of Formulas I or II or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of the present invention are prepared as set forth in Chart I hereof wherein X, R, $R_1$ and $R_2$ have the meanings defined in Formula I.

An alcohol or thiol of the formula $R_1XH$ is reacted with chlorosulfonyl isocyanate in an inert organic solvent, such as THF, $Et_2O$ or $CH_2Cl_2$ at room temperature or preferably colder ($\leq 0°$ C.). The resulting chlorosulfonyl carbamate or carbamothioate may precipitate out of solution or it can be triturated with a nonpolar solvent such as hexanes. The chlorosulfonyl carbamate or carbamothioate can be isolated or it can be used as is and reacted with any alcohol of the formula $R_2OH$ in an inert organic solvent such as THF, $Et_2O$ or $CH_2Cl_2$ at ambient temperature in the presence of an acid scavenger such as triethylamine. The oxysulfonyl carbamate thus formed can be converted to its base salt by reacting with an appropriate metal or amine base. The base salt can then be reacted with an appropriate alkylating agent such as R-I wherein R is as defined above only R is other than hydrogen and I is iodine.

The thiols and alcohols, $R_1XH$ and $R_2OH$, used in preparing the compounds of this invention are known in the art or prepared by procedures generally known in the art.

The specific examples set forth below further illustrate the preparation of compounds of general Formula I.

EXAMPLE 1

Synthesis of
2,6-Bis(1-methylethyl)phenyl[[2,6-bis(1-methylethyl)phenoxy]sulfonyl]carbamate A solution of 2,6-bis(1-methylethyl)phenyl (chlorosulfonyl) carbamate (16.0 g, 50 mmoles) in 150 mL THF was added dropwise to a solution of 2,6-diisopropyl phenol (8.92 g, 50 mmoles) and triethylamine (7.0 mL, 50 mmoles) in 200 mL THF at room temperature under an atmosphere of $N_2$. The mixture was stirred for 16 hours, concentrated in vacuo, and the residue partitioned between $H_2O$ and $CH_2Cl_2$. The organic layer was dried with $MgSO_4$, filtered, and evaporated to give an oily tan solid. The oily solid was taken up in 10% EtOAc/hexanes and the solvent decanted away from the oily impurities, then evaporated to give an off-white solid. The solid was triturated with hexanes to give the title compound, mp 124°-128° C.

EXAMPLE 2

Synthesis of
2,6-Bis(1,1-dimethylethyl)-4-methylphenyl(phenoxysulfonyl)carbamate A solution of 2,6-bis(1,1-dimethylethyl)-4-methylphenyl (chlorosulfonyl)carbamate (10.0 g, 27.6 mmoles) in 120 mL THF was added dropwise to a solution of phenol (2.60 g, 27.6 mmoles) and triethylamine (3.85 mL, 27.6 mmoles) in 200 mL THF at room temperature under an atmosphere of $N_2$. The mixture was stirred for 16 hours, concentrated, and partitioned between $H_2O$ and EtOAc. The organic layer was dried with $MgSO_4$, filtered, and evaporated to give a yellow oil which was triturated with hexanes to give an off-white solid. Chromatography of this solid ($SiO_2$, 5% EtOAc/hexanes) gave the title compound (5.64 g), mp 122°-125° C.

EXAMPLE 3

Synthesis of
2,6-Bis(1,1-dimethylethyl)-4-methylphenyl[(hexyloxy)sulfonyl]carbamate A solution of 2,6-bis(1,1-dimethylethyl)-4-methylphenyl(chlorosulfonyl)carbamate (5.0 g, 13.8 mmoles) in 80 mL THF was added dropwise to a solution of n-hexanol (1.41 g, 13.8 mmoles) and excess triethylamine (~3 mL) in 80 mL THF at room temperature under an atmosphere of $N_2$. The mixture was stirred for 16 hours and then concentrated in vacuo. The residue was partitioned between 1N HCl and EtOAc and the EtOAc layer was dried with $MgSO_4$, filtered, and evaporated to give a clear oil which was triturated with hexanes to give 2.97 g of the title compound as a white solid, mp 118 121° C.

EXAMPLE 4

2,6-Bis(1,1-dimethylethyl)-4-methylphenyl[(dodecyloxysulfonyl]carbamate

When in the general procedure of Example 3, an appropriate amount of n-dodecyl alcohol is substituted for n-hexanol, the title compound was obtained, mp 85°-87° C.

EXAMPLE 5

Synthesis of Dodecyl
[[2,6-bis(1-methylethyl)phenoxy]sulfonyl]carbamate

A solution of n-dodecyl(chlorosulfonyl)carbamate (5.0 g, 15.2 mmoles) in 80 mL THF was added dropwise to a solution of 2,6-diisopropyl phenol (2.72 g, 15.2 mmoles) and excess triethylamine in 100 mL THF at room temperature under an atmosphere of $N_2$. The mixture was stirred for 16 hours and then concentrated in vacuo. The residue was partitioned between 1N HCl and EtOAc. The organic layer was dried with $MgSO_4$, filtered, and evaporated to give a clear oil. Chromatography ($SiO_2$, 5% EtOAc/hexanes) gave 4.26 g of the title compound as a waxy solid; mp 32°-35° C.

EXAMPLE 6

Methyl[[2,6-bis(1-methylethyl)phenoxy]sulfonyl]carbamate

When in the general procedure of Example 5, an appropriate amount of methyl(chlorosulfonyl)carbamate was substituted for n-dodecyl(chlorosulfonyl)carbamate, the title compound was obtained, mp 92°-95° C.

EXAMPLE 7

2,6-Bis(1-methylethyl)phenyl[(hexyloxy)sulfonyl]carbamate

When in the general procedure of Example 1, an appropriate amount of n-hexanol was substituted for 2,6-diisopropyl phenol, the title compound was obtained, mp 110°-111° C.

EXAMPLE 8

2,6-Bis(1-methylethyl)phenyl](dodecyloxy)sulfonyl]carbamate

When in the general procedure of Example 1, an appropriate amount of n-dodecanol was substituted for 2,6-diisopropyl phenol, the title compound was obtained, mp 69°-72° C.

EXAMPLE 9

2,6-Bis(1,1-dimethylethyl)phenyl[[2,6-bis(1-methylethyl)phenoxy]sulfonyl]carbamate When in the general procedure of Example 1, an appropriate amount of 2,6-bis(1,1-dimethylethyl)phenyl(chlorosulfonyl)carbamate was substituted for 2,6-bis(1-methylethyl)phenyl(chlorosulfonyl) carbamate, the title compound was obtained, mp 109°-114° C.

EXAMPLE 10

[1,1':3',1"-Terphenyl]-2'-yl[(dodecyloxy)sulfonyl]carbamate

A solution of [1,1':3',1"-terphenyl]-2'-yl (chlorosulfonyl)carbamate (5.0 g, 12.9 mmoles) in 75 mL THF was added dropwise to a solution of n-dodecyl alcohol (2.4 g, 12.9 mmoles) and triethylamine (1.3 g, 12.9 mmoles) in 100 mL THF at ~15° C. under an atmosphere of $N_2$. The mixture was allowed to warm to room temperature for 16 hours, then concentrated in vacuo and partitioned between $H_2O$ and EtOAc. The EtOAc layer was dried with $MgSO_4$ and evaporated to give a white solid. Chromatography ($SiO_2$, 10% EtOAc/hexanes) gave 2.95 g of the title compound, mp 124°-126° C.

The following Examples 11 to 16 describe the synthesis of the carbamates useful in the preparation of final products of this invention.

EXAMPLE 11

Synthesis of Methyl(chlorosulfonyl)carbamate (Ref. Org. Syn. 56, 40(1977)

A solution of methanol (10.2 mL, 252 mmoles) in 15 mL toluene was added dropwise to a solution of chlorosulfonyl isocyanate (22.0 mL, 252 mmoles) in 75 mL toluene at 0° C. The mixture was removed from the cooling bath and stirred for one-half hour at room temperature, then cooled to 0° C. and 65 mL ice cold hexanes was added. The white precipitate was collected by filtration and washed two times with a small amount of cold hexanes and dried in vacuo to give 33.0 g of a white solid, mp 72°-74° C.

EXAMPLE 12

Synthesis of Dodecyl(chlorosulfonyl)carbamate (R. Graf, Chem. Ber., 96, 56 (1963)

A solution of n-dodecyl alcohol (10.7 g, 57.4 mmoles) in 100 mL $Et_2O$ was added dropwise to a solution of chlorosulfonyl isocyanate (5.0 mL, 57.4 mmoles) in 100 mL $Et_2O$ at ~15° C. under an atmosphere of $N_2$. The resulting mixture was stirred for 2 hours and concentrated in vacuo. The residue was triturated with cold hexanes to give a white solid and collected by filtration to give 19.12 g of a white solid, mp 62°-63° C.

EXAMPLE 13

Synthesis of 2,6-Bis(1-methylethyl)phenyl(chlorosulfonyl)carbamate (Ref: Phosphorus and Sulfur, 19, 167 (1984))

A solution of 2,6-diisopropyl phenol (37.1 mL, 0.2 moles) in 200 mL $Et_2O$ was added dropwise to a solution of chlorosulfonyl isocyanate (17.4 mL, 0.2 moles) in 200 mL $Et_2O$ at −15° C. and then stored at −15° C. under an atmosphere of $N_2$ for 16 hours, then concentrated to give an orange oil and triturated with hexanes and quickly collected by filtration to give 55.64 g (87%) of product as a white solid.

EXAMPLE 14

Synthesis of 2,6-Bis(1,1-dimethylethyl)phenyl(chlorosulfonyl)carbamate (Ref: Phosphorus and Sulfur, 19 167, (1984))

A solution of 2,6-di-t butyl phenol (20.63 g, 0.1 mole) in 100 mL $Et_2O$ was added dropwise to a solution of chlorosulfonyl isocyanate (8.7 mL, 0.1 moles) in 100 mL $Et_2O$ at −15° C. (acetone/ice bath) under an atmosphere of $N_2$, stirred for 1 hour, and then concentrated in vacuo to leave a thick gel. It was then triturated with hexanes and filtered to give 28.60 g (82%) of the title compound as a white solid, mp 135°-137° C.

EXAMPLE 15

Synthesis of 2,6-Bis(1,1-dimethylethyl)-4-methylphenyl(chlorosulfonyl)carbamate (Ref: Phosphorus and Sulfur, 19 167 (1984))

A solution of 2,6-di-t-butyl-4-methyl phenol (22.04 g, 0.1 moles) in 100 mL $Et_2O$ was added dropwise to a solution of chlorosulfonyl isocyanate (8.7 mL, 0.1 moles) in 100 mL $Et_2O$ at −15° C. under an atmosphere of $N_2$. The resulting gel was stirred for 2 hours, concentrated, and triturated with hexanes to give 26.82 g (74%) of the title compound as a white solid.

EXAMPLE 16

Synthesis of [1,1]:3'1"-Terphenyl]-2'-yl(chlorosulfonyl)carbamate

A solution of 2,6-diphenylphenol (25.0 g, 0.101 moles) in 250 mL $Et_2O$ was added dropwise to a solution of chlorosulfonyl isocyanate (9.7 mL, 0.112 mmoles) in 100 mL hexanes at −15° C. under an atmosphere of $N_2$. The resulting white suspension was allowed to warm to room temperature over 2 hours and was then concentrated in vacuo and triturated with ice-cold hexanes. Vacuum filtration afforded 41.28 g of a white solid, mp 159°-162° C.

The following compounds can be prepared by following the general procedure of Example 3 and substituting the appropriate carbamate and alcohol:

2,6-bis(1,1-dimethylethyl)phenyl [[2,6-bis(1,1-dimethylethyl)phenoxy]sulfonyl]carbamate, 2,6-dimethylphenyl [(2,6-dimethylphenoxy)sulfonyl]carbamate, 2,6-bis(1-methylethyl)phenyl [(2,6-dimethylphenoxy)sulfonyl]carbamate, 2,6-bis(1,1-dimethylethyl)phenyl [(2,6-dimethylphenoxy)sulfonyl]carbamate,
2,6-bis(1,1-dimethylethyl)phenyl (dodecyloxysulfonyl)carbamate,
2,6-bis(1-methylethyl)phenyl [(1-methyltridecyloxy)sulfonyl]carbamate,
2,6-bis(1,1-dimethylethyl)phenyl [(1-methyltridecyloxy)sulfonyl]carbamate,
2,6-bis(1-methylethyl)phenyl [(1-methylundecyloxy)sulfonyl]carbamate,
2,6-bis(1,1-dimethylethyl)phenyl [(1-methylundecyloxy)sulfonyl]carbamate,
2,4,6-trimethoxyphenyl [[2,6-bis(1-methylethyl)phenoxy]sulfonyl]carbamate,
2,4,6-trimethoxyphenyl (dodecyloxysulfonyl)carbamate,
2,4,6-trimethoxyphenyl [(1-methyltridecyloxy)sulfonyl]carbamate,
2,4,6-trimethoxyphenyl [(1-methyl(undecyloxy)sulfonyl]carbamate,
2,6-bis(1-methylethyl)phenyl [(2,4,6-trimethoxyphenoxy)sulfonyl]carbamate, and
2,6-bis(1,1-dimethylethyl)phenyl [(2,4,6-trimethoxyphenoxy)sulfonyl]carbamate.

EXAMPLE 17

2,6-Bis(1-methylethyl)phenyl(phenoxysulfonyl)carbamate

When in the general procedure of Example 1, an appropriate amount of phenol was substituted for 2,6-diisopropyl phenol, the title compound was obtained, mp 100°–104° C.

EXAMPLE 18

2,6-Bis(1-methylethyl)phenyl[(2,6-dimethylphenoxy)sulfonyl]carbamate

When in the general procedure of Example 1, an appropriate amount of 2,6-dimethyl phenol was substituted for 2,6-diisopropyl phenol, the title compound was obtained, mp 134°–137° C.

EXAMPLE 19

2,6-Bis(1-methylethyl)phenyl[(2,6-dimethoxyphenoxy)sulfonyl]carbamate

When in the general procedure of Example 1, an appropriate amount of 2,6-dimethoxy phenol was substituted for 2,6-diisopropyl phenol, the title compound was obtained, mp 132°–133° C.

EXAMPLE 20

2,6-Bis(1-methylethyl)phenyl][(2,4-difluorophenoxy)sulfonyl]carbamate

When in the general procedure of Example 1, an appropriate amount of 2,4-difluoro phenol was substituted for 2,6-diisopropyl phenol, the title compound was obtained, mp 78°–81° C.

EXAMPLE 21

2,6-Bis(1-methylethyl)phenyl[(2,4,6-trimethoxyphenoxy)sulfonyl]carbamate

When in the general procedure of Example 1, an appropriate amount of 2,4,6-trimethoxy phenol was substituted for 2,6-diisopropyl phenol, the title compound was obtained, mp 130°–132° C.

EXAMPLE 22

2,6-Bis(1-methylethylphenyl[(2,6-difluorophenoxy)sulfonyl]carbamate

When in the general procedure of Example 1, an appropriate amount of 2,6-difluoro phenol was substituted for 2,6-diisopropyl phenol, the title compound was obtained, mp 137°–142° C.

EXAMPLE 23

2,6-Bis(1-methylethyl)phenyl[(hexadecyloxy)sulfonyl]carbamate

When in the general procedure of Example 1, an appropriate amount of hexadecanol was substituted for 2,6-diisopropyl phenol, the title compound was obtained, mp 69°–72° C.

EXAMPLE 24

2,6-Bis(1-methylethyl)phenyl[[2,6-bis(1,1-dimethylethyl)phenoxy]sulfonyl]carbamate When in the general procedure of Example 1, an appropriate amount of the sodium salt of 2,6-bis(1,1-dimethylethyl)phenol was substituted for 2,6-diisopropyl phenol, the title compound was obtained, mp 173°–176° C.

EXAMPLE 25

Synthesis of 2,6-dimethoxyphenyl[(2,6-dimethoxyphenoxy)sulfonyl]carbamate

A solution of triethylamine (4.97 mL, 36 mmol) and 2,6-dimethoxy phenol (10.0 g, 65 mmol) in 100 mL THF was added dropwise to a solution of chlorosulfonyl isocyanate (2.96 mL, 34 mmol) in 100 mL THF at 0° C. The resulting mixture was allowed to warm to room temperature and stirred for 16 hours. Concentrated in vacuo and partitioned between 1N HCl and ethyl acetate. The organic layer was dried with MgSO$_4$, filtered, and evaporated to give a tan solid. Recrystallized from hexanes to give the title compound, mp 167°–170° C.

EXAMPLE 26

2,6-Bis(1,1-dimethylethyl)phenyl[(2,6-bis(1,1-dimethylethyl)phenoxy)sulfonyl]carbamate When in the general procedure of Example 25, an appropriate amount of 2,6-bis(1,1-dimethylethyl) phenol was substituted for 2,6-dimethoxy phenol, the title compound was obtained, mp 195°–197° C.

EXAMPLE 27

Synthesis of 2,6-bis(1-methylethyl)phenyl[[2,6-bis(1-methylethyl)phenoxy]sulfonyl]carbamate, 2-hydroxy-N,N,N-trimethylethanaminium salt A solution of 2,6-bis(1-methylethyl)phenyl[[2,6-bis(1-methylethyl)phenoxy]sulfonyl]carbamate (5.0 g, 10.8 mmol) in 75 mL THF was added dropwise to an aqueous solution (3.98 g, 45% soln., 10.8 mmol) of choline bicarbonate. After complete addition, the reaction was heated to reflux for ½ hour, cooled to room temperature and evaporated to give a thick oil. Triturated with Et$_2$O to give the title compound, mp 139°–141° C.

EXAMPLE 28

Synthesis of 2,6-bis(1-methylethyl)phenyl[[2,6-bis(1-methylethyl)-phenoxy]sulfonyl]carbamate, monosodium salt A solution of 2,6-bis(1-methylethyl)phenyl[[2,6-bis(1-methylethyl)phenoxy]sulfonyl]carbamate (20.0 g, 43.3 mmol) in 200 mL THF was added dropwise to a suspension of hexane washed sodium hydride (1.73 g, 60% dispersion in mineral oil, 43.3 mmol) in 100 mL THF at 0° C. under a nitrogen atmosphere. Warmed to room temperature and stirred for 2 hours. Filtered, concentrated, and redissolved in 300 mL water. The aqueous mixture was filtered and concentrated to about half original volume. Lyophilized to give the title compound, mp 247°–250° C.

EXAMPLE 29

Synthesis of S-2,6-bis(1-methylethyl)phenyl (chlorosulfonyl)carbamothioate

A solution of 2,6-diisopropyl thiophenol in 125 mL hexane was added dropwise to a solution of chlorosulfonyl isocyanate in 100 mL hexane at −15° C. under an atmosphere of nitrogen. Stirred for 4 hours and filtered to give the title compound as an off-white solid, mp 119°–121° C.

EXAMPLE 30

Synthesis of S-[2,6-bis(1-methylethyl)phenyl][(dodecyloxy)sulfonyl]carbamothioate A solution of S-2,6-bis(1-methylethyl)phenyl (chlorosulfonyl)carbamothioate (3.0 g, 9.0 mmol) in 50 mL THF was added dropwise to a solution of dodecyl alcohol (1.66 g, 9.0 mmol) and triethylamine (0.9 g, 9.0 mmol) in 100 mL THF at −15° C. under an atmosphere of nitrogen. Allowed to warm to room temperature and stirred for 16 hours. Concentrated in vacuo and partitioned between water and ethyl acetate. Dried the organic layer (MgSO4), filtered, and evaporated to give a clear oil. Chromatography gave the title compound as a white solid, mp 83°–84° C.

EXAMPLE 31

Synthesis of 2,6-bis(1-methylethyl)phenyl[[2,6-bis(1-methylethyl)-phenoxy]sulfonyl]methyl carbamate A solution of 2,6-bis(1-methylethyl)phenyl [[2,6-bis(1-methylethyl)phenoxy]sulfonyl]carbamate (5.0 g, 10.8 mmol) and methyl iodide (1.69 g, 11.9 mmol) in 100 mL acetonitrile was stirred at −15° C. under an atmosphere of nitrogen. 1,8-Diazabicyclo[5.4.0]undec-7-ene (1.78 mL, 11.9 mmol) was added in one portion and the resulting solution was warmed to room temperature and stirred for 16 hours. Concentrated in vacuo and partitioned the residue between 1N HCl and ethyl acetate. Dried the organic layer over MgSO4, filtered, and evaporated to give an orange oil. Triturated with hexane to give an off-white solid. Recrystallized from ethyl acetate/hexanes (1:9) to give the title compound, mp 95°–101° C.

CHART I

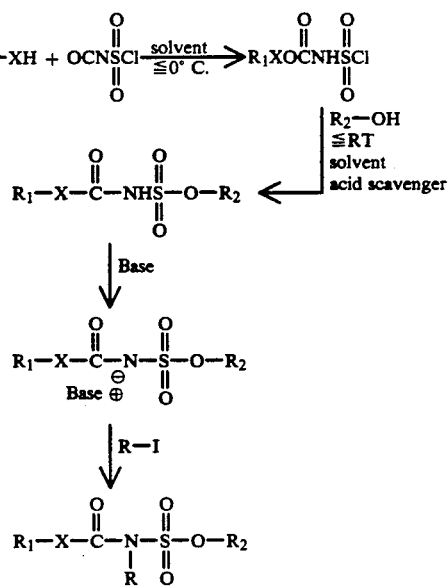

We claim:
1. A compound of the formula

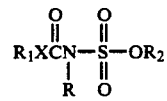

wherein X is oxygen or sulfur; wherein R is hydrogen, a straight or branched alkyl group having from 1 to 8 carbon atoms or benzyl; wherein R1 is selected from
(a) phenyl which is unsubstituted or is substituted with from 1 to 3 substituents selected from
   phenyl,
   an alkyl group having from 1 to 6 carbon atoms and which is straight or branched,
   an alkoxy group having from 1 to 6 carbon atoms and which is straight or branched;
   phenoxy,
   hydroxy,
   fluorine,
   chlorine,
   bromine,
   trifluoromethyl,
   —COOH,
   —COOalkyl wherein alkyl has from 1 to 4 carbon atoms and is straight or branched,
   —(CH2)pNR3R4 wherein p is zero or one, and each of R3 and R4 is selected from hydrogen or a straight or branched alkyl group having 1 to 4 carbon atoms;
(b) 1- or 2-naphthyl which is unsubstituted or is substituted with from 1 to 3 substituents selected from
   phenyl,
   an alkyl group having from 1 to 6 carbon atoms and which is straight or branched,
   an alkoxy group having from 1 to 6 carbon atoms and which is straight or branched;
   phenoxy,
   hydroxy,
   fluorine, chlorine,
bromine,
nitro,
trifluoromethyl,
—COOH,
—COOalkyl wherein alkyl has from 1 to 4 carbon atoms and is straight or branched,
—$(CH_2)_pNR_3R_4$ wherein p, $R_3$, and $R_4$ have the meanings defined above;

wherein $R_2$ is selected from (a) phenyl which is unsubstituted or is substituted with from 1 to 3 substituents selected from
phenyl,
an alkyl group having from 1 to 6 carbon atoms and which is straight or branched,
an alkoxy group having from 1 to 6 carbon atoms and which is straight or branched;
phenoxy,
hydroxy,
fluorine,
chlorine,
bromine,
trifluoromethyl,
—COOH,
—COOalkyl wherein alkyl has from 1 to 4 carbon atoms and is straight or branched,
—$(CH_2)_pNR_3R_4$ wherein p is zero or one, and each of $R_3$ and $R_4$ is selected from hydrogen or a straight or branched alkyl group having 1 to 4 carbon atoms;

(b) 1- or 2-naphthyl which is unsubstituted or is substituted with from 1 to 3 substituents selected from
phenyl,
an alkyl group having from 1 to 6 carbon atoms and which is straight or branched,
an alkoxy group having from 1 to 6 carbon atoms and which is straight or branched;
phenoxy,
hydroxy,
fluorine,
chlorine,
bromine,
nitro,
trifluoromethyl,
—COOH,
—COOalkyl wherein alkyl has from 1 to 4 carbon atoms and is straight or branched,
—$(CH_2)_pNR_3R_4$ wherein p, $R_3$, and $R_4$ have the meanings defined above;

(c) the group

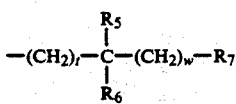

wherein t is zero or 1 to 4; w is zero or 1 to 4 with the proviso that the sum of t and w is not greater than 5; $R_5$ and $R_6$ are independently selected from hydrogen or alkyl having from 1 to 6 carbon atoms, or when $R_5$ is hydrogen, $R_6$ can be selected from the groups defined for $R_7$; and $R_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH_2)_pNR_3R_4$ wherein P, $R_3$, and $R_4$ have the meanings defined above; or (d) a straight or branched hydrocarbon chain having from 1 to 20 carbon atoms and which is saturated or contains from 1 to 3 double bonds; and pharmaceutically acceptable acid salts thereof with the proviso that:
(i) one of R1 or R2 is phenyl or substituted phenyl and
(ii) the following compounds are excluded:

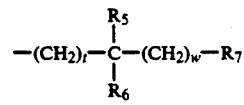

2. A compound of claim 1 wherein $R_1$ is phenyl.
3. A compound of claim 1, wherein $R_1$ is phenyl disubstituted in the 2,6-positions.
4. A compound of claim 1 wherein $R_2$ is phenyl.
5. A compound of claim 1 wherein $R_2$ is phenyl disubstituted in the 2,6-positions.
6. A compound of claim 1 wherein each of $R_1$ and $R_2$ is phenyl.
7. A compound of claim 1 wherein each phenyl disubstituted in the 2,6-positions.
8. A compound of claim 1 which is:
2,6-Bis(1-methylethyl)phenyl[[2,6-bis(1-methylethyl)phenoxy]sulfonyl]carbamate,
2,6-Bis(1,1-dimethylethyl)-4-methylphenyl (phenoxysulfonyl)carbamate,
2,6-Bis(1,1-dimethylethyl)-4-methylphenyl[(hexyloxy)sulfonyl]carbamate,
2,6-Bis(1,1-dimethylethyl)-4-methylphenyl[-(dodecyloxy-sulfonyl]carbamate,
2,6-Bis(1-methylethyl)phenyl[(hexyloxy)sulfonyl]carbamate,
2,6-Bis(1-methylethyl)phenyl](dodecyloxy)sulfonyl]carbamate,
2,6-Bis(1,1-dimethylethyl)phenyl[[2,6-bis(1-methylethyl)phenoxy]sulfonyl]carbamate.
9. A compound of claim 1 which is 2,6-bis(1-methylethyl)phenyl[[2,6-bis(1-methylethyl)phenoxy]sulfonyl]carbamate, monosodium salt.

* * * * *

UNITED STATES PATENT AND TRADEMARK OFFICE
CERTIFICATE OF CORRECTION

PATENT NO. : 5,245,068
DATED : September 14, 1993
INVENTOR(S) : Joseph A. Picard, et al It is certified that error appears in the above-identified patent and that said Letters Patent is hereby corrected as shown below:

Column 18, lines 25-29, delete " 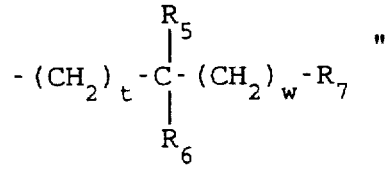 ".

and insert --

| $\underline{R_1}$ | $\underline{R_2}$ |
|---|---|
| 4-ClPh | 4-ClPh |
| 2,4,6-triClPh | $CH_3$ |
| 2,6-di-Cl-4-Ph-Ph | $n$-$C_3H_7$ |

--.

Column 18, line 38, insert --is-- between "phenyl disubstituted".

Signed and Sealed this

Seventh Day of June, 1994

Attest:

BRUCE LEHMAN

Attesting Officer

Commissioner of Patents and Trademarks